US008105273B1

(12) United States Patent
Fox

(10) Patent No.: US 8,105,273 B1
(45) Date of Patent: Jan. 31, 2012

(54) SELF FLUSHING DUAL COMPARTMENT CONTAINER

(76) Inventor: Carla Y Fox, Crest Hill, IL (US)

(*) Notice: Subject to any disclaimer, the term of this patent is extended or adjusted under 35 U.S.C. 154(b) by 85 days.

(21) Appl. No.: 12/479,388

(22) Filed: Jun. 5, 2009

(51) Int. Cl.
*A61M 5/14* (2006.01)
(52) U.S. Cl. ........................................................ 604/80
(58) Field of Classification Search .................. 604/80
See application file for complete search history.

(56) References Cited

U.S. PATENT DOCUMENTS 5,088,994 A * 2/1992 Porat et al. .................. 604/408
6,146,360 A * 11/2000 Rogers et al. ................ 604/151
6,261,262 B1 7/2001 Briggs et al.

OTHER PUBLICATIONS

Ross Easy-Feed® Enteral Nutrition Bag With Preattached Ross Gravity Feeding Set No. ROS00056 sold by Home Care Essentials, Jul. 5, 2006, http://www.homecareessentials.com/ros00056.html.
Ross Flexiflo® Top-Fill Enteral Nutrition Bag with Preattached Quantum Pump Set & Flush bag, ROS50606, Jul. 5, 2006, http://www.homecareessentials.com/rofltoennuba.html.
Ross Flexiflo® Patrol® Pump Set with Piercing Pin No. ROS52040 sold by Home Care Essentials, Jul. 5, 2006, http://www.homecareessentials.com/flpapusetpip.html.

* cited by examiner

*Primary Examiner* — Nicholas Lucchesi
*Assistant Examiner* — Jason Flick
(74) *Attorney, Agent, or Firm* — Patents and Licensing LLC; Daniel W Juffernbruch

(57) ABSTRACT

This single unit, known as a self flushing duel compartment container, can be used with or without an electrical feeding pump. It will perform a dual, fluid composition administration process, which would usually require two separate units to perform. Thus eliminating the need for the use of a secondary unit needed to follow the administrations seen in the existing products used primary/secondary fluid delivery technique. Two separate compartments are capable of retaining their own fluid composition within the boundary of it's own separate compartment separated by an air tight, sealed section of the single unit that divides this single unit into two separate compartments. Each compartment leads into a section of thermoplastic tubing, which eventually forms a pre-attached junction tubing similar to the "Y", shaped tubing that becomes a single much longer section of thermoplastic tubing. Fluids from both compartments (side A) and (side B) will flow through this thermoplastic tubing, one following the other, when the fluid compositions are administered to the receiver of the contents contained in this new invention.

7 Claims, 4 Drawing Sheets

SELF FLUSHING DUAL COMPARTMENT CONTAINER

BACKGROUND OF THE INVENTIONS

1. Technical Field

The present inventions relate to containers and, more particularly, relate to containers with tubing.

2. Description of the Related Art

Conventional flexible bags or rigid containers used to administer a primary fluid composition followed by the administration of a clear fluid composition, used for flushing either parenterally or gastro intestinally, are administered by way of two separate single compartment flexible bags or rigid containers. These two separate containers are currently referred to as a primary and secondary flexible bag or rigid container. These two single unit containers from which these fluid compositions are administered are usually connected to an electrical feeding pump with each unit having totally separate containers and their own individual, flexible thermoplastic tubing through which the fluids separately flow to reach the patient or other destination. When the fluid composition being administered from the primary container requires a secondary; fluid composition to be administered such as sterile water, or normal saline for a parenteral flush and tap water or bottled water for a gastro intestinal flush; needed to clear the primary fluid composition from it's original place from which it was previously administered, it usually requires that the flush be administered thru a separate flexible bag of rigid container or other fluid collection devices used for flushing, thus as mentioned before requires two different containers. Both the primary and the secondary flexible or rigid containers are currently hung in a separate location in close proximity of each other on a separate hook or hanging device which helps to complete the two container, fluid composition administration/flushing process.

Current pairs of conventional single unit flexible or rigid containers used together presently contain two separate fluid compositions that are at some point intended to be mixed and simultaneously administered together, thus administering one fluid composition mixture leaving no uncombined fluid composition behind to be administered separate from the other. An example of this occurs when a secondary clear fluid composition is needed to flush out the existing primary fluid composition currently being administered, thus current single unit single compartment flexible or rigid containers must receive a secondary clear fluid compositional flush from a secondary single or multiple compartment unit.

While such fluid administration and post flushing systems function generally satisfactorily, there are some disadvantages with the existing products. For example, the medical personnel administering the primary parenteral or gastrointestinal fluid compositions must separately hang a second, separate container used for flushing or flush from another separate fluid collection device, such as a bottle of normal saline or the current 60 cc syringe used to flush gastro-intestinal feeding tubes after the completion of a scheduled feeding. Administering a secondary flush and/or clear fluid composition administration is not only time consuming, but is also not cost effective because it requires that the health care provider use some source of energy other than manual labor and that they purchase an additional flexible bag or rigid container, or other device used for a secondary administration of clear fluids used to administer the flush, such as a 60 cc syringe used for flushing after enteral feedings.

Thus it is desired to provide an improved container.

SUMMARY OF THE INVENTIONS

An object of the present inventions is to provide an easy to use feeding system.

A further object of the present inventions is to provide a unitary feeding bag with two chambers.

Another further object of the present inventions is to provide a feeding bag with an automatic flushing capability.

Another object of the present inventions is to make it easy to flush with or without the use of an electrical pump or other energy source other than manual labor.

A further other object of the present inventions is to reduce human error of forgetting to flush.

An additional object of the present inventions is to reduce human error of forgetting to flush on time.

Another additional object is to provide an environmentally "green" invention that will eliminate the excessive use of electricity currently needed to operate pre-existing self flushing devices.

The details of the preferred embodiments and these and other objects and features of the inventions will be more readily understood from the following detailed description when read in conjunction with the accompanying drawings wherein:

BRIEF DESCRIPTION OF THE DRAWINGS

In the accompanying drawings that form part of the specification, and in which like numerals are employed to designate like parts throughout the same.

DETAILED DESCRIPTION OF THE PREFERRED EMBODIMENTS

Figure 1:
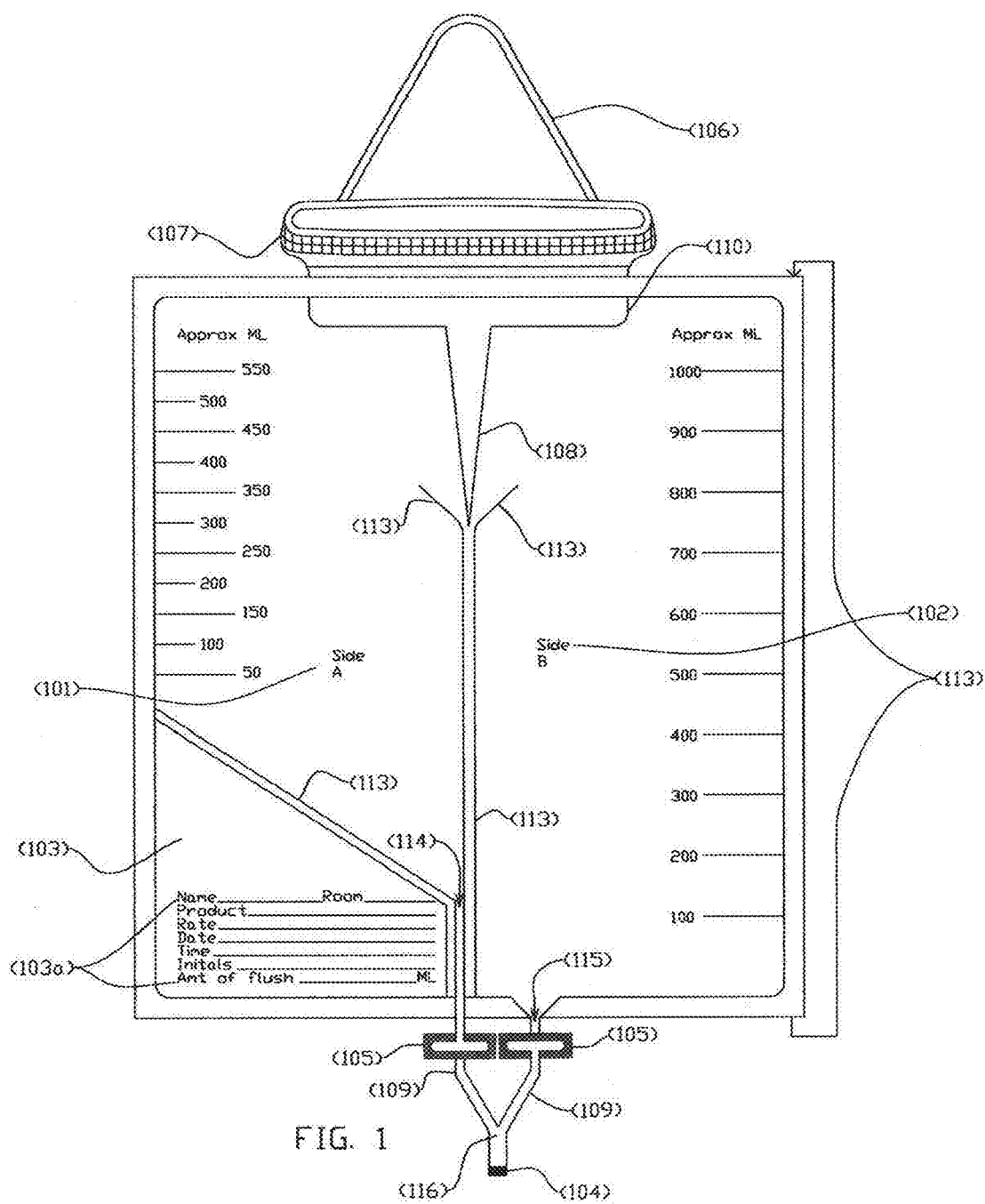
FIG. 1 illustrates a perspective view of the new self flushing dual compartment container according to the present inventions.

Thus it is desired to provide a new and improved single unit, flexible or rigid container comprising two separate compartments embodied into the same single unit container, that can administer a primary fluid composition followed by a secondary clear fluid composition used for flushing, hereafter known as the self flushing dual compartment container.

Further, a single unit that provides both primary and secondary fluid composition administrations from a single unit can have a tremendous impact on the amount of the current hospital admissions involving patients admitted with the diagnosis of dehydration and urinary tract infections. Dehydration and urinary tract infections are usually caused by a decreased fluid intake, or lack of adequate fluid intake being administered to the patient. This can be largely contributed to healthcare staff shortages and the current unrealistic nurse to patient ratios, seen across the country in thousands of healthcare facilities.

With the current nursing shortages it would be much more easier for one nurse to fill the primary compartment (side A) with about 100 cc to about 500 cc of an enteral feeding composition, and the secondary compartment (side B) with an about 50 cc to about 1000 cc of water flush both embodied into the same unit and hung per gravity instead of using the time it takes to hang—two separate containers and connecting and programming them through the current electrical feeding pumps needed for flushing by the current inventions. This would also eliminate the nurse forgetting to push adequate amounts of fluids by hand held fluid delivery devices such as a 6 occ syringe currently used for flushing after enteral feedings. Also this is not an adequate amount of fluid as would be delivered by this new invention—which will also help to cut down on the number of patents being admitted with dehydration and urinary tract infections currently seen today due to a lack of adequate fluid intake, thus decreasing the hospital admissions contributing to the huge savings of healthcare dollars now paid by government healthcare programs such as Medicaid and Medicare. It would also absorb some of the cost paid by the patient's private insurance companies and out of pocket healthcare cost that are currently accrued by the patent or healthcare facility. The embodiments of the present inventions are environmentally conscious because they can be used with or without electricity.

The improved design of the present invention accommodates administration of a variety of fluid compositions being known as parenteral fluids, enteral fluids, whole blood, red blood cell components and the like to be administered through this new invention with certain conventional components. The various fluid compositions can be administered to patents having an intravenous or gastrointestinal site into which the fluid compositions can be instilled, one following the other without the use of an additional, secondary container used for flushing that now requires the use of a pump powered by some form of energy other than manual labor, which is much more expensive to operate and also a time consuming process currently employed with the present inventions.

A flush is a rapid flow of water or other liquid employed for the removal of a primary substance that is no longer desired to remain in its original place of instillation. The flush is administered buy way of a flushing device, which is needed to accurately transmit the water or liquid to the area where the original substance is to be removed. An example of a much-needed flush would be similar to the function of the kidneys in the human body. Water is needed to flush the waste products from the body to aid in the continuation of life and good optimal health. No one can survive without the flushing of water through the urinary system, which could not function without the flushing of water through the kidneys.

The self flushing duel compartment container causes that water to be self administered following the same pathway as the primary fluid composition, therefore flushing and removing the primary fluid composition so that it does not remain in the same place too long, thus causing it to also become unwanted waste. Inadequate fluid intake of water can cause major health problems and prolonged lack of fluid intake can cause dehydration and urinary tract infections, which are two major causes of hospitalizations seen in the elderly population. Continued lack of adequate fluid intake can also lead to kidney failure and the need for kidney dialysis which help contribute to Government Healthcare Programs—losing billions of dollars each year. These governmental programs can greatly benefit from the use of self flushing duel compartment container. This new invention can be used in nursing homes across the county, seeing that most of these patients are recipients of enteral feedings and rely on the funds of governmental health care benefits such as Medicare and other government assisted programs. Also this new invention can be of medical use in areas where electrical power is not available—such as in times of disasters.

FIG. 1 illustrates a perspective view of the new self flushing dual compartment container according to the present inventions. An oval shaped, partition separator cap in place in the closed position, shown in FIG. 2 as a cross sectional view. The container in FIG. 1 is shown without a pre-attached gravity feeding set connected. Proceeding down from top to bottom of the illustration in FIG. 1 is first the plastic hook 106 used to hang the container, connected to 110 the base of the new oval shaped, partition separator cap which is where the female grooved receptive piece 211 is found, covered by 107 the lid containing the male insertion piece 212, the lid being shown in the closed position in FIG. 1 and in the partially closed position in FIG. 2, seen as a cross sectional view of the lid and the base of the new oval shaped, partition separator cap. The two plastic panels 113 shown already sealed together around the edges to make up the embodiment of the entire container and is sealed to form the labeling area under first side compartment 101, are also sealed surrounding the distal end of the female grooved receptive piece 108, which is attached to the base 110 of the new oval shaped, partition separator cap in, thus creating an air tight seal between first side compartment 101 and second side compartment 102 also shown in FIG. 1. Directly under first side compartment 101 is the flattened, sealed together area 103, used for labeling referred to as 103a. Continuing down both side compartments 101 and 102 as shown in FIG. 1, at the distal end of both side compartments 114 and 115, is the pre-attached junction tubing 109 with a conventional slide clamp 105 in place. Terminating at the end of the pre-attached junction tubing is the optional, rubber tipped female insertion site 104, where a conventional pre-attached gravity feeding set can be connected either during the manufacturing process or afterwards which can be purchased with a piercing pin in place.

Now referring to the illustrated in FIG. 1 The new invention of the self flushing duel compartment container hereafter, periodically referred to as "the new invention," can be connected to several different flexible, thermoplastic tubing administration or feeding sets that currently exist, The administration or feeding sets may be of any appropriate conventional or special design used for intravenous or gastrointestinal administration, as described below.

Abbott Laboratories, 100 Abbott Road, Abbott Park, Ill. 60064-3500, U.S.A. currently sells one known Pre-attached Gravity Feeding Set in the U.S.A. which seems to be disclosed by U.S. Pat. No. 6,261,262 to Briggs et al. This conventional thermoplastic tubing set can be pre-connected during the manufacturing process or a similar feeding set manufactured by Ross currently known as the Ross Flexiflo Patrol Pump Set with Piercing Pin. No. ROS52040 sold by Home Care Essentials, which can be used to spike the pre-attached flexible junction illustrated in FIG. 1, 104 located at the distal portion of the new invention. In such case the self flushing duel compartment container of FIG. 1, will need to be manufactured already pre-filled with a fluid composition used to be delivered by way of an intravenous, gastrointestinal or other known route that may not be specified in this document.

Both conventional sets mentioned in the above paragraph can be connected to the pre-attached flexible junction 104 located at the distal portion of the new invention FIG. 1. To aid in this presentation, I will be detailing this new invention without the current pre-attached Gravity Feeding Sets, as noted in the above paragraph.

The flattened area 103, located directly underneath first side compartment 101 of the new invention FIG. 1, is used for the labeling information 103a. This area is sealed together at an angle descending from left to right when viewed by the viewer. It provides a flat surface 103 on which information can be written. The information asked for should include the patient's name and room number, fluid composition to be administered from first side compartment 101, rate of administration, date and time container is prepared, amount of water flush in second side compartment 102, to be administered following the completion of first side compartment 101 and the initials of the person preparing and administering the contents contained in the self flushing duel compartment container shown in FIG. 1.

This area 103 is needed to ensure the proper administration to the right patient or other desired destination. This information can be pre-printed onto the flattened informational area 103, or on a pre-printed, self-adhesive label which can be attached to the distal portion of this flattened informational area 103a. Both of which should contain lines and headings on which to record the information mentioned in the above paragraph.

Further description of FIG. 1 is a front view of the new invention also referred to as the self flushing duel compartment container which is comprised of two flexible plastic panels 113 connected together peripherally and midline forming a partition between both side compartments 101 and 102, all of the underlined areas in this paragraph being a part of the same two flexible plastic panels 113, excluding the openings from which the oval shaped, partition separator cap, comprising 107 and 110, is permanently connected to the top portion of the embodiment of the new invention and also excluding the openings where the pre-attached junction tubing 109 is permanently connected to the embodiment of the new invention. One tubing being connected to the distal portion 114 of first side compartment 101 and the other tubing being connected to the distal portion 115 of second side compartment 102, both tubing then joining together to form a single lumen tubing 116, thus becoming the distal end of the pre-attached junction tubing 104.

Figure 2:
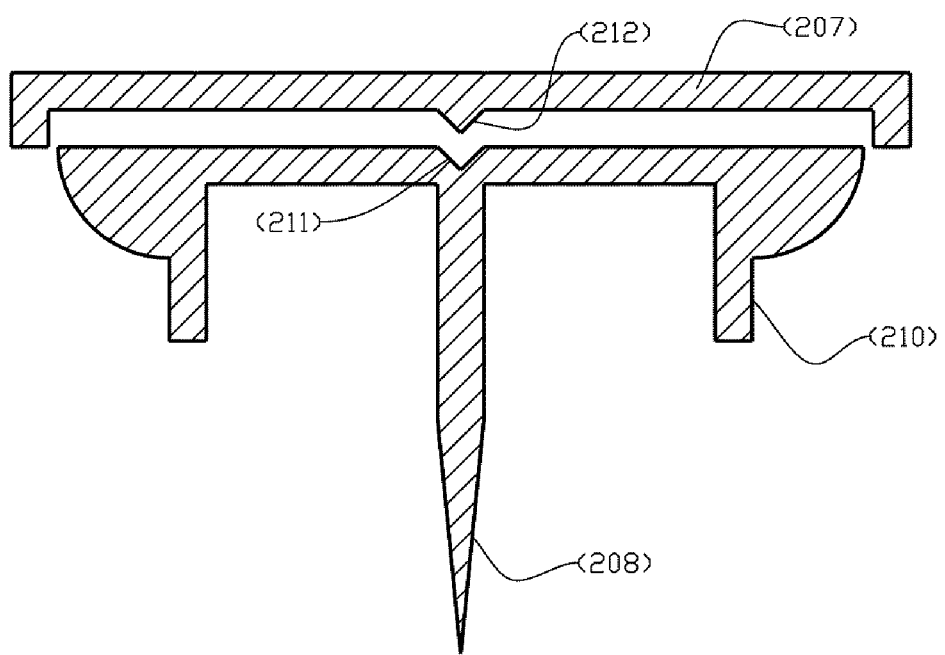
FIG. 2 illustrates a cross-sectional view of the new oval shaped, partition separator cap according to the present inventions.

FIG. 2 illustrates a cross-sectional view of the new oval shaped, partition separator cap according to the present inventions. An oval shaped, partition separator cap is shown with the lid 207 partially opened to fit together with the base 210 of the new oval shaped partition separator cap. Also shown is the female grooved receptive piece 211 and the male insertion piece 212.

FIG. 2 illustrates a cross-sectional view of the new oval shaped, partition separator cap 107 and 110 in the partially opened position showing the female grooved receptive piece 211, which runs midline inside the base leading to the distal end 208 of the new oval shaped, partition separator cap comprising 107 and 110. The cap when closed properly forms a seal with the male insertion piece 212, which runs midline down the center of the top portion of the lid 207. When the male, insertion piece 212 is inserted into the female grooved receptive piece 211, which occurs after the cap is tightly closed, an airtight seal is created, thus keeping the fluids contained in the first side compartment FIG. 1, 101 separated from the fluids contained in the second side compartment FIG. 1, 102, of the new self flushing duel compartment container.

Figure 3:
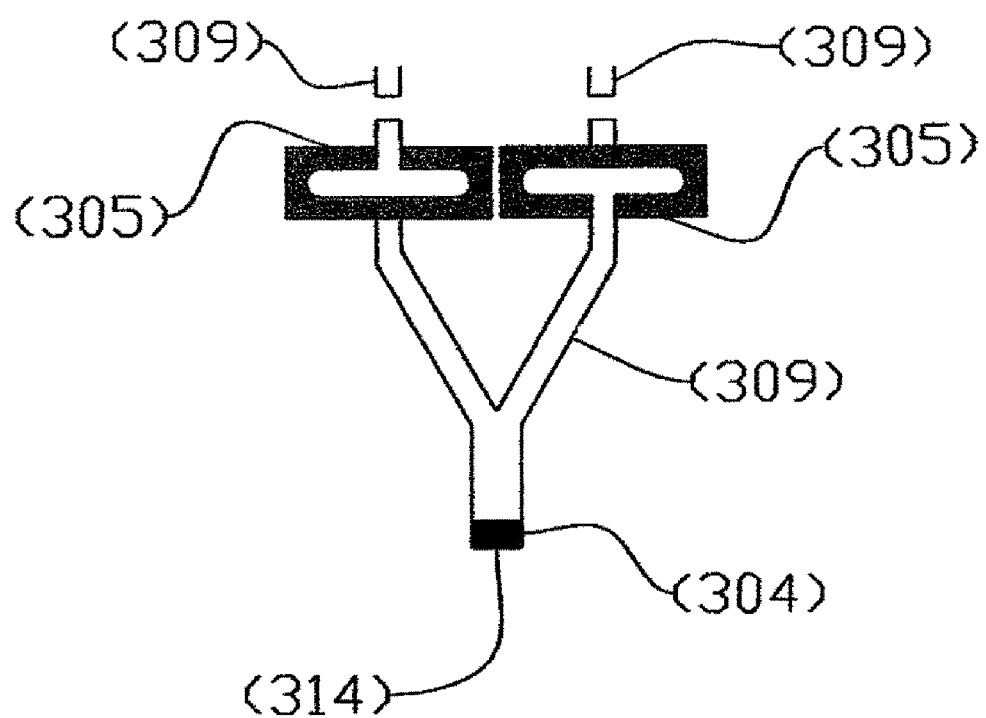
FIG. 3 illustrates an enlarged view of the pre-attached junction tubing with the optional, rubber tipped female insertion site attached according to the present inventions.

FIG. 3 illustrates an enlarged view of the pre-attached junction tubing with the optional, rubber tipped female insertion site attached according to the present inventions. The pre-attached junction tubing 309 has an optional, rubber tipped female insertion site 304, attached. As stated in above with respect to FIG. 1, the optional, rubber tipped female insertion site 304, is used if the new self flushing dual compartment container illustrated in FIG. 1 does not require a conventional pre-attached gravity feeding set, without the piercing pin.

The pre-attached junction tubing 309 can be constructed with various flexible or rigid plastic materials. The type of plastic material selected will depend on the type of administration tubing set that will be connected to the distal end of the tubing 304.

Attached to the pre-attached junction tubing 309 is a view of the slide clamp 305, located on both sides of the tubing 309. The slide clamp 305 can be obtained as a part of many conventional fluid administration sets currently being used. Before each fluid administration process can take place the entire tubing 309 exiting from the first distal end 114 and, the tubing exiting from the second distal end 115 seen in FIG. 1, should remain clamped during the instillation of the fluid composition into (side A) 101 and the water used for flushing into (side B) 102. After both sides are filled with the desired amount of fluid compositions the slide clamp 305 located on the tubing exiting from first distal end 114, is moved into an open position to allow the tubing 109 to be primed. The conventional slide clamp 305 or similar device is always used in the priming process during the start of each fluid administration. Priming is a process in which the fluid is allowed to free flow through the flexible tubing until it reaches the distal end of the tubing, removing the air from the primed tubing.

During the priming of the tubing exiting from the first distal end 114, the slide clamp located on the tubing exiting from the distal end of 115 remains clamped until all air is completely removed from tubing connected to (Side A) is primed and being administered to the patient, the slide clamp 305 on the tubing exiting from the distal end of 115 should then be moved into an open position to allow the water flush contained in (side B) to start automatically flowing following the completion of the fluid composition from (side A). The above process takes place to insure the proper administration of the fluid compositions to the patient or other desired destination.

This slide clamp 305 is used to close the second side compartment 102, to allow the priming process of the first side compartment 101. Once the priming process is complete, the side clamp 305 located on the tubing exiting from the distal end of 115 is removed so that both compartments are allowed to drain in successive order, the primed fluid in first side compartment 101 draining first. The nutritional composition and water flush should flow successively if the first distal end 114 is higher than the second distal end 115 so that gravity causes the pressure in the tubing from the higher (side A) to be pulled into the tubing from the lower (side B) thus impeding the flow of the water flush from (side B) until the pressure is removed following the completion of the nutritional composition administration from (side A). The slide clamp 305 helps to assist with the functioning of this new invention in FIG. 1. Although exemplary slide clamps 305 are illustrated in the various drawings, any device capable of temporarily pinching off the tubing on both sides, including the two human fingers can be used if a clamp is not readily available.

Figure 4:
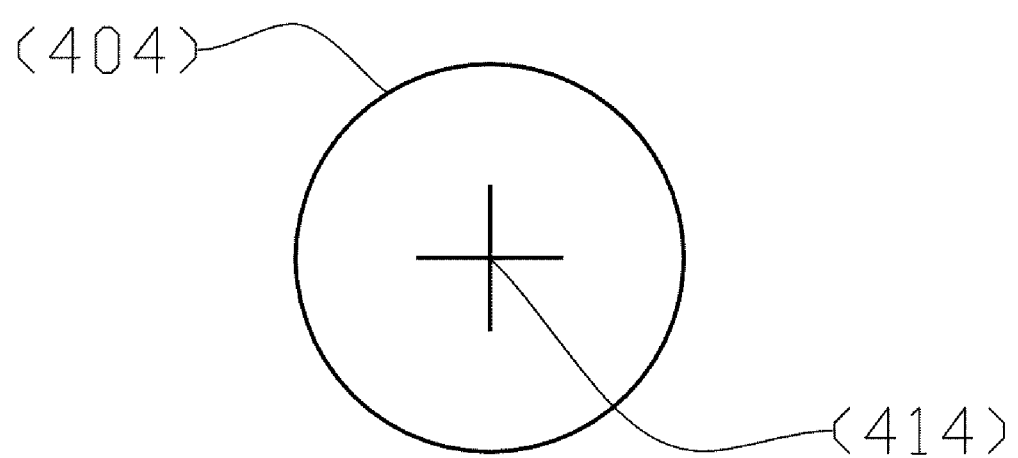
FIG. 4 illustrates an enlarged view of the rubber tipped female insertion site showing a close up view of the entry into the insertion port located at the distal end of the pre-attached junction tubing according to the present inventions.

FIG. 4 illustrates an enlarged view of the rubber tipped female insertion site showing a close up view of the entry into the insertion port located at the distal end of the pre-attached junction tubing according to the present inventions. The rubber tipped female insertion site 404 is shown in close up of the entry into the insertion port 414 located at the distal end of the pre-attached junction tubing as illustrated in FIG. 3, 304 which is where a conventional Gravity Feeding Set with a piercing pin attached, can be connected into the insertion port 414, creating an air tight seal, thus aiding in the passage of the contents contained in the new self flushing dual compartment container illustrated in FIG. 1, to be passed through the attached flexible tubing into the receiving source.

The distal end of the pre-attached junction tubing 404 has the optional rubber tipped female insertion port 414 shown in FIG. 4. This feature is used to attach the piercing pin, which is connected to a detachable administration set, one being known as the current invention of the Ross Flexiflo Patrol Pump Set with Piercing Pin. The piercing pin is inserted into the female insertion port 414, thus is attaching it to the new invention.

Referring back to FIG. 1, in such a case as mentioned in the above paragraph, if the manufacturer has chosen to pre-fill and pre-seal the self flushing duel compartment container FIG. 1, with a ready to use fluid composition contained in (side A) 101 and a ready to use water flush contained in (side B) 102, therefore the container is spiked with an administration set similar to the Ross Flexiflo Patrol Pump Set with Piercing Pin. It is recommended that a more rigid plastic material be used when the pre-attached junction tubing 109 has optional the female insertion site 104 attached so that a piercing pin will have a more stable connection with the new invention, thus creating an air tight seal between the piercing pin and the distal end of pre-attached junction tubing 104. This new invention has no need for a female insertion site 104 if it has a Pre-attached Gravity Feeding Set already in place, which is not illustrated in this document being a part of a known current invention.

While the embodiments of the present inventions are susceptible implementation in many different forms and can be used by many different industries, the accompanying drawings and specification disclose example forms used in an example application industry. The invention is not intended to be limited to the embodiments or uses so described.

For ease of description the use of this invention is described detailing a specific procedural use involving the medical industry. It will be understood, however that this invention may be made, stored, transported, used and sold other than detailed in this description.

Figures illustrating the container show some elements that are known and that will be recognized by one skilled in the art. The detailed descriptions of such elements are not necessary for the understanding and primary functioning of the invention but are presented here related to its conjunctional use with the invention.

This invention incorporates certain conventional components that although the details are not fully illustrated or described, will be apparent to those having skill in the art and an understanding of the necessary functions of such components.

Although the inventions have been described and illustrated in the above description and drawings, it is understood that this description is by example only, and that numerous changes and modifications can be made by those skilled in the art without departing from the true spirit and scope of the inventions. Although the examples in the drawings depict only example constructions and embodiments, alternate embodiments are available given the teachings of the present patent disclosure.

What is claimed is:

1. A self flushing bag, comprising: a first side compartment integrally connected to a second side compartment, wherein the first side compartment comprises a first distal end; and the second side compartment comprises a second distal end lower than the first distal end, wherein the first distal end and the second distal end are joined at a Y junction, comprising Y junction tubing, below the first and second distal ends to accommodate gravity drainage of a fluid out from both the first and second side compartments and arranged to provide a successive capability of automatically draining, wherein after the first side compartment is opened at the first distal end and begins to drain, the second side compartment is opened at the second distal end before the first side compartment is emptied and wherein the second side compartment only begins to drain after the first side compartment is emptied; further comprising a tube coupled to the Y junction tubing at a proximal end of the tube; and a stop mechanism comprising a first and second user-operated mechanical closure device, applicable to at least one side of the Y junction tubing such that the tube is primed with a medically acceptable composition from one of the first and second side compartments by, first, applying the stop mechanism to one side of the Y junction tubing and, then, second, releasing the stop mechanism from the Y junction tubing after the composition begins to flow to automatically allow fluid from the other of the first and second side compartments to flow sequential to said flow of said composition.

2. A self flushing bag according to claim 1,
wherein the first user operated mechanical closure device comprises a first clamp between the first distal end and the Y junction tubing to open the first side compartment at the first distal end; and
wherein the second user operated mechanical closure device comprises a second clamp between the second distal end and the Y junction tubing to open the second side compartment at the second distal end.

3. A self flushing bag according to claim 1, further comprising a pair of flexible plastic panels connected peripherally and midline embodying said first side compartment and said second side compartment, forming a partition between said first side compartment and said second side compartment.

4. A self flushing bag according to claim 1, further comprising a partition separator cap further comprising a base, wherein said base further comprises a female grooved receptive piece, and a lid, wherein said lid further comprises a male insertion piece which runs midline down the center of the top portion of said lid.

5. A self flushing bag according to claim 4, wherein said male insertion piece compliments said female grooved receptive piece.

6. A self flushing bag according to claim 4, wherein when said lid is inserted into said base forms an airtight seal.

7. A self flushing bag according to claim 1, wherein the first side compartment contains a nutrition composition; wherein the second side compartment contains a flush fluid; and wherein said tube comprises a feeding tub.

\* \* \* \* \*